US00PP16178P2

(12) United States Plant Patent
Betts

(10) Patent No.: US PP16,178 P2
(45) Date of Patent: Jan. 3, 2006

(54) ***IRIS* PLANT NAMED 'MAINESTREAM SPRING'**

(50) Latin Name: *Iris hybrida*
Varietal Denomination: Mainestream Spring

(76) Inventor: Mary S. Betts, 315 Bridge Rd., Parkman, ME (US) 04443-3330

( * ) Notice: Subject to any disclaimer, the term of this patent is extended or adjusted under 35 U.S.C. 154(b) by 195 days.

(21) Appl. No.: 10/911,929

(22) Filed: Jul. 30, 2004

(51) Int. Cl.
*A01H 5/00* (2006.01)

(52) U.S. Cl. ..... Plt./310

(58) Field of Classification Search ..... Plt./310
See application file for complete search history.

*Primary Examiner*—Anne Marie Grunberg
(74) *Attorney, Agent, or Firm*—Penny J. Aguirre

(57) ABSTRACT

'Mainestream Spring' is an interspecific *Iris* hybrid that exhibits the unique characteristic of having spring foliage that emerges gold in color and is further characterized by its violet blue flowers borne on branched flower stems combined with a vigorous growth habit.

2 Drawing Sheets

Botanical classification: *Iris hybrida.*
Cultivar designation: 'Mainestream Spring'.

CROSS REFERENCE TO A RELATED APPLICATION

This application is co-pending with U.S. Plant patent application Ser. No. 10/903,311 filed for a sibling entitled Iris Plant Named 'Mainestream Tempest'.

BACKGROUND OF THE INVENTION

The present invention, *Iris* 'Mainestream Spring', relates to a new and distinct cultivar of *Iris*, botanically known as an *Iris* hybrid, more specifically an interspecific *Iris* hybrid, and is hereinafter referred to as 'Mainestream Spring'.

The inventor discovered the new cultivar, 'Mainestream Spring', in a seedling bed in her nursery in Parkman, Me. in 1993. The seedlings in the bed were derived from seed collected from open pollinated plants of *Iris* 'Orville Fay' (unpatented), a cultivar of Siberian *Iris* (hybrid origin). 'Mainestream Spring' was initially selected as one of 8 seedlings that exhibited the unique characteristic of having spring foliage that emerged gold in color and later turned green as the season progressed. On further observation, it became apparent that the selected seedlings were interspecifc hybrids, with an unnamed plant of *Iris versicolor* growing next to the pod parent as the apparent pollen parent. The selected seedlings were observed to have the plant habit, growth habit, and flowering stem branching more typical of the pollen parent, *Iris versicolor*, and flowers that combined the characteristics of the pollen and pod parent in terms of form, size, color, and markings. The 8 seedlings evaluated could be distinguished from one another in several aspects, including plant height, degree of yellow coloration to the foliage and flower coloration. 'Mainestream Spring' was selected from the group of seedlings as unique for its large blue flowers borne on branched flower stems, its vigorous growth habit, and its gold spring foliage.

The closest comparison other than the sibling of 'Mainestream Spring', 'Mainestream Tempest' is *Iris*

'Neidenstein', an *Iris* selected in Germany and determined to be a interspecific hybrid between a Siberian *Iris* 'Niklassee' (unpatented) and *Iris versicolor* 'Claret Cup' (unpatented). 'Mainestream Spring' differs from 'Neidenstein' in flower color and by having wider foliage, and greater overall vigor. 'Mainestream Spring' differs from 'Mainestream Tempest' primarily in having lavender blue flowers whereas 'Mainestream Tempest' has purple flowers and in having more intensely colored gold foliage in spring.

Asexual reproduction of the new cultivar was first accomplished by rhizome division in 1994 in Parkman, Me. by the discoverer. The characteristics of the new cultivar have been determined to be stable and reproduced true to type in successive generations.

SUMMARY OF THE INVENTION

The following traits have been repeatedly observed and represent the characteristics of the new cultivar. These attributes in combination distinguish 'Mainestream Spring' as a new and unique cultivar of *Iris:*

1. 'Mainestream Spring' is an interspecific hybrid combining characteristics derived from *Iris* 'Orville Fay' a cultivar of Siberian *Iris* and *Iris versicolor.*
2. In spring, the center leaves of each fan emerge yellow in color, gradually turning green as the season progresses. This foliage coloration is unique and not present in any Siberian *Iris* cultivar or selection of *Iris versicolor* known to the inventor. The foliage of a similar hybrid, 'Niklassee', exhibits a similar coloration, however the foliage of 'Mainestream Tempest' is wider.
3. The flower stems are multi-branched with 2–3 branches per stem. The branching is more typical of *Iris versicolor*, however 'Orville Fay' typically has only one branch.
4. 'Mainestream Spring' has a vase-shaped plant form, similar to what is typical of *Iris versicolor*, rather than the upright plant form exhibited by *Iris* 'Orville Fay'.

5. The flowers of 'Mainestream Spring' appear in June and are lavender blue in color with a signal that is yellow and white with deep purple veins.
6. 'Mainestream Spring' has a very vigorous growth rate, exceeding the growth rate of both the pollen and pod parent.

BRIEF DESCRIPTION OF THE DRAWING

The accompanying colored photographs illustrate the overall appearance and distinct characteristics of the new *Iris*. The photographs were taken of three year-old plants of 'Mainestream Spring' as grown outdoors in Plymouth, Minn.

Figure 1:
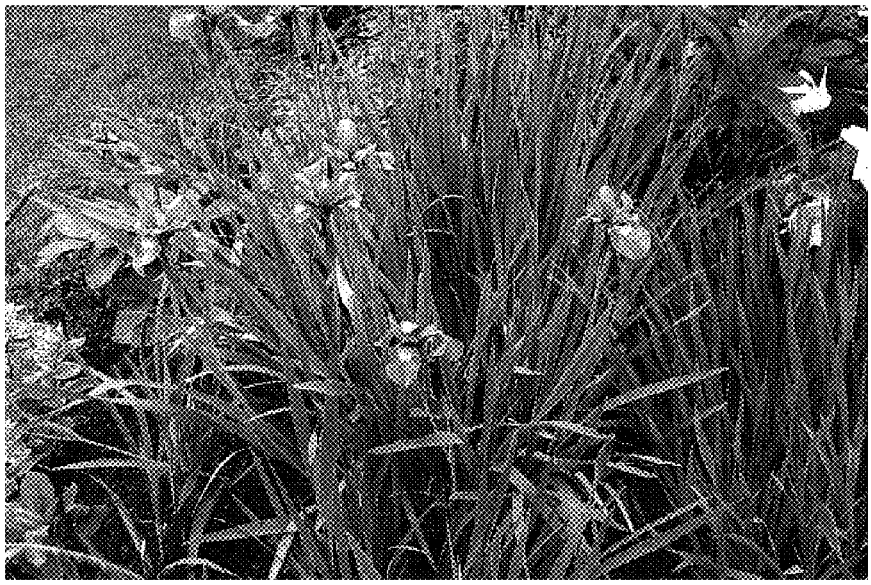
FIG. 1 was taken in June and provides an overall view of new cultivar in bloom.
Figure 2:
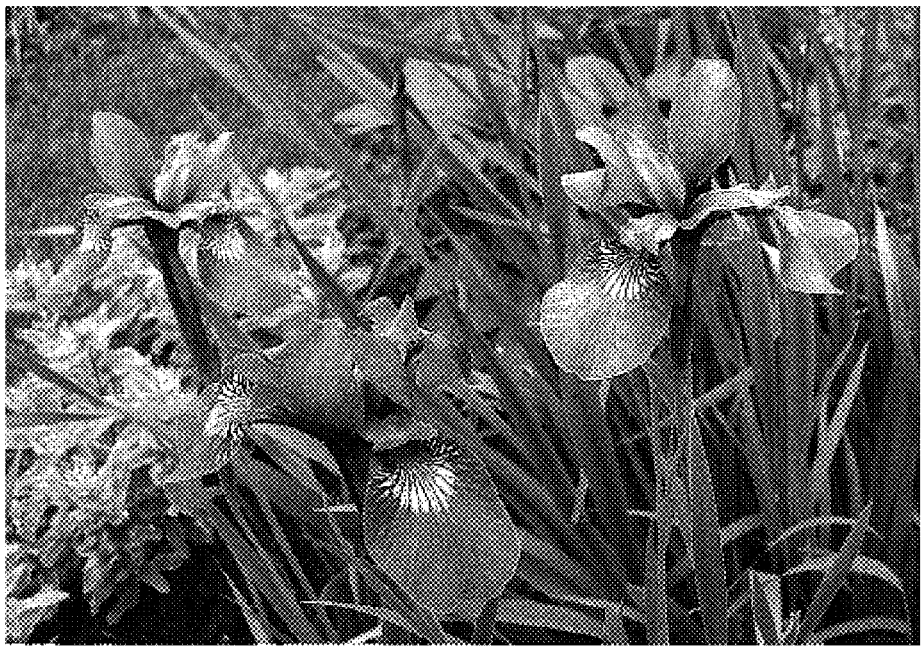
Figure 3:
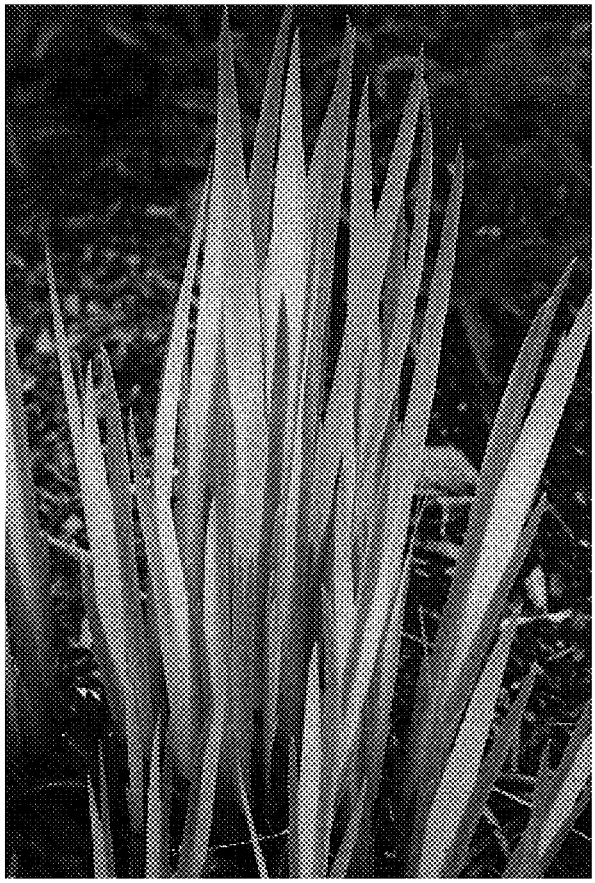

The photograph in FIG. 2 is of a close-up view of the flowers of 'Mainestream Spring' and The photograph in FIG. 3 is a close-up of the foliage taken in May.

The colors in the photographs are as close as possible with the photographic and printing technology utilized. The color values cited in the detailed botanical description accurately describe the colors of the new *Iris*.

DETAILED BOTANICAL DESCRIPTION OF THE PLANT

The following is a detailed description of 3 year-old plants of the new cultivar from a as grown outdoors in Plymouth, Minn. and Parkman, Me. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Mainestream Spring' is a cultivar of *Iris* of hybrid origin.

Parentage: Derived from seed collected from open pollinated plants of *Iris* 'Orville Fay' (unpatented), a cultivar of Siberian *Iris* (hybrid origin). The pollen parent is an unnamed plant of *Iris versicolor*.

*Blooming period.*—About 2 weeks in June in Maine and Minnesota.

*Plant habit.*—Herbaceous perennial, clump-forming, upright vase-shaped.

*Height and spread.*—Reaches about 91 cm in height (36"), one fan will multiple to form 3 to 7 fans per year depending on conditions. A one-fan division will spread to about 45 cm (18") in 2 years.

*Hardiness.*—Zone 4 (possibly 3).

*Culture.*—Full sun to light shade, moist soils of moderate fertility.

*Diseases and pests.*—No unique susceptibility or resistance to diseases or pests has been observed for 'Mainestream Spring'.

*Root description.*—Rhizomes with fibrous roots ranging from fleshy to wiry. Rhizome is 0.5 to 1 cm in width and up to about 7 cm in length, N167C in color.

*Propagation.*—Rhizome division in early spring or late summer through fall.

*Root development.*—Development in containers has not been established. Rhizomes will increase at a rate of 3 to 7 per rhizome per growing season in Northern U.S. climates when grown in moderately fertile, evenly moist soils in full sun.

*Growth rate.*—Vigorous in comparison to typical beardless *iris* species and cultivars.

Foliage description:

*Leaf shape.*—Lanceolate.

*Leaf division.*—Simple.

*Leaf base.*—Sheathed to base of rhizome.

*Leaf apex.*—Acute.

*Leaf venation.*—Longitudinal, parallel, not prominent, same color as leaves.

*Leaf margins.*—Entire.

*Leaf attachment.*—Sheathed.

*Leaf arrangement.*—Comprises a fan with new growth emerging from center of fan.

*Leaf orientation.*—Held upright and slightly pendulant once matured.

*Leaf surface.*—Slightly glaucous.

*Leaf color.*—Young leaves (upper and lower surface), emerge 1B, gradually turning 144A. Mature leaves (upper and lower surface) 137B. Lower base of outer leaves is 71B in color extending about 5 cm from attachment to rhizome.

*Leaf size.*—Up to about 7 to 35 cm in length, 0.5 to 1.75 cm in width.

*Leaf quantity.*—About 5 leaves per fan.

Flower scape description:

*Scape shape.*—Round, slightly ovoid, pithy.

*Scape number.*—One per mature fan under normal growing conditions.

*Scape posture.*—Straight, held upright at about 70 to 90° from horizontal.

*Scape size.*—About 91 cm in length with branches about 20 to 26 cm in length, about 1 mm in width at base and tapeing to about 4 mm at apex.

*Scape color.*—144A.

*Scape surface.*—Glabrous, slight sheen.

*Scape branching.*—Typically 2 branches occasionally 3, internodes of 10 to 14 cm if third branch exists.

*Scape leaves.*—1 per branch point and typical 2 from base, 137B in color, 12 to 36 cm in height, up to 2 cm in width, clasping base base, acute apex.

Flower description:

*Inflorescence type.*—Perianth tubular comprised of six segments (petals): 3 outer petals form falls narrowing into a haft, 3 inner petals form standards. Petaloid style arms branch over the falls.

*Lastingness of inflorescence.*—About 2 weeks from first opening bloom to fading of last opening bloom, individual blooms last about 4 days.

*Flower fragrance.*—None detected.

*Flower number.*—5 to 7 per scape; 3 per terminal and 2 per branch.

*Flower bud shape.*—Oblong.

*Flower bud size.*—Up to about 8 cm in length and up to about 0.8 cm in width.

*Flower bud color.*—Upper portion (about ⅓) 93A, lower portion (about ⅔) is 144A marked with 93A.

*Spathes.*—1 to 2, enclose ovary, about 4 to 6 cm in length, about 1.0 to 1.5 cm in width, base is clasping, apex is acute, 144B in color with slight overlay of N77A, becoming papery and 176C in color.

*Flower size.*—Fully open: About 7 to 8 cm in height from base of receptacle and about 10 to 11 cm in width.

*Color of standards and falls.*—(Upper and lower surface). — Open 93A (violet-blue), fading to 96D (becomes more blue). Signal extends about 3 cm from base, 7D (yellow) with N89C (violet-blue) veining, surrounding by an area 155C (white) with N79A (purple) veining.

*Size of falls.*—About 6 cm in height, 4 cm in width at apex and 1 cm in width at base.

*Shape of falls*.—Spatulate.

*Apex of falls.*—Rounded.

*Base of falls.*—Blunt.

*Size of standard.*—About 5 cm in length and 3 cm in width, base is about 1 cm in length and 0.5 cm in width.

*Shape of standards.*—Obovate with narrow base.

*Apex of standards.*—Rounded.

*Base of standards.*—Blunt.

Reproductive organs:

*Gynoecium.*—Style; 3-branched, showy, petaloid, 1.3 cm in width, 4 cm in height, 93B to 93C in color when opening, fading to 93D, ridge has overlay of 84A. Style flaps; 2, together 1.3 cm in width and 1 cm in height, 93B in color with veining N88B. Stigma; petaloid, about 3 mm in height, 5 mm in width, triangular in shape 93B in color. Ovary; inferior, 2 to 3 cm in height, about 1 cm in width, with stipe 2 to 4 cm in height, 2.5 to 4 mm in width, 144B in color.

*Androcoecium.*—Stamens; 3, borne from base of falls. Filament; about 1 cm in length, up to 2 mm in width, 83A in color. Anthers; about 1.3 cm in length, 93A in color, basifixed, longitudinal dehiscence. Pollen; moderately abundant, 1D in color.

*Seed.*—Capsule development has been observed, presumed sterile. When present, capsules are flattened and about 3 cm in length and about 0.7 cm in width. The color is 177B.

It is claimed:

1. A new and distinct cultivar of *Iris* plant named 'Mainestream Spring' as herein illustrated and described.

* * * * *